(12) United States Patent
Colson

(10) Patent No.: US 10,373,388 B2
(45) Date of Patent: Aug. 6, 2019

(54) AUGMENTED-REALITY TEST METHOD AND TEST BENCH FOR A TURBINE ENGINE

(71) Applicant: Safran Aero Boosters SA, Herstal (BE)

(72) Inventor: Jean-François Colson, Herve (BE)

(73) Assignee: SAFRAN AERO BOOSTERS SA, Herstal (BE)

( * ) Notice: Subject to any disclaimer, the term of this patent is extended or adjusted under 35 U.S.C. 154(b) by 130 days.

(21) Appl. No.: 15/590,719

(22) Filed: May 9, 2017

(65) Prior Publication Data

US 2017/0323484 A1 Nov. 9, 2017

(30) Foreign Application Priority Data

May 9, 2016 (BE) .................................. 2016/5327

(51) Int. Cl.
*G01M 15/14* (2006.01)
*G06T 19/00* (2011.01)
(Continued)

(52) U.S. Cl.
CPC ........... *G06T 19/006* (2013.01); *G01M 15/14* (2013.01); *G01N 21/8803* (2013.01);
(Continued)

(58) Field of Classification Search
CPC ..... G06T 19/006; G06T 15/205; G06T 7/001; G06T 2200/04; G06T 2207/30108;
(Continued)

(56) References Cited

U.S. PATENT DOCUMENTS 7,126,558 B1* 10/2006 Dempski .............. G02B 27/017
345/8
7,565,269 B2* 7/2009 Parfitt ..................... G01L 5/133
702/182
(Continued)

FOREIGN PATENT DOCUMENTS

EP 2642331 A1 9/2013
EP 3009826 A1 4/2016
FR 3017711 A1 8/2015

OTHER PUBLICATIONS

Search Report dated Jan. 26, 2017 from parent Belgium Application No. 201605327.

*Primary Examiner* — Freddie Kirkland, III
(74) *Attorney, Agent, or Firm* — James E. Walton

(57) ABSTRACT

A method for testing a turbojet engine for an aircraft in a U-shaped or open-air test bench includes: (a) visual inspection of the test bench and of the turbojet engine; and (b) testing of the turbojet engine in the test bench. During the test, the turbojet engine bears test equipment with sensors, other sensors being housed in the test bench. The test bench includes an augmented-reality system performing the step of (a) visual inspection in the test bench in order to detect a possible major anomaly in the test bench. The step of (a) visual inspection is intended to check the conformity of the test conditions, and especially those of the test equipment or that of the test bench as a whole. The method performs the step of (b) testing only in the absence of an anomaly.

19 Claims, 3 Drawing Sheets

(51) Int. Cl.
*G01N 21/88* (2006.01)
*G06T 7/00* (2017.01)
*G06T 15/20* (2011.01)
*G06T 7/73* (2017.01)
*F01D 21/00* (2006.01)

(52) U.S. Cl.
CPC ......... *G01N 21/8806* (2013.01); *G06T 7/001* (2013.01); *G06T 15/205* (2013.01); *F01D 21/003* (2013.01); *F05D 2260/12* (2013.01); *F05D 2260/81* (2013.01); *F05D 2270/8041* (2013.01); *G06T 7/74* (2017.01); *G06T 2200/04* (2013.01); *G06T 2207/30108* (2013.01)

(58) Field of Classification Search
CPC .. G06T 7/74; G01N 21/8803; G01N 21/8806; G01M 15/14; F05D 2270/8041; F05D 2260/81; F05D 2260/12; F01D 21/003
See application file for complete search history.

(56) References Cited

U.S. PATENT DOCUMENTS

| | | | |
|---|---|---|---|
| 8,485,038 B2 * | 7/2013 | Sengupta | F01D 21/003 73/661 |
| 9,251,582 B2 * | 2/2016 | Lim | G06F 17/30247 |
| 9,952,438 B1 * | 4/2018 | Broadhead | G06F 3/011 |
| 2007/0276601 A1 | 11/2007 | Parfitt | |
| 2009/0154293 A1 | 6/2009 | Sengupta | |
| 2014/0185912 A1 * | 7/2014 | Lim | G06F 17/30247 382/141 |

* cited by examiner

AUGMENTED-REALITY TEST METHOD AND TEST BENCH FOR A TURBINE ENGINE

This application claims priority under 35 U.S.C. § 119 to Belgium Patent Application No. 2016/5327, filed 9 May 2016, titled "Augmented-Reality Test Method and Test Bench for a Turbine Engine," which is incorporated herein by reference for all purposes.

BACKGROUND

1. Field of the Application

The present application relates to testing of a turbine engine. In particular, the present application concerns a method for testing a turbine engine in a test bench. A further subject matter of the present application lies in a computer program and also a computer which are used in the context of testing a turbine engine.

2. Description of Related Art

When a turbojet engine is designed, produced and maintained, a number of tests are carried out on a specific test bench. The functioning of the turbojet engine is verified under actual usage conditions in order to demonstrate the reliability thereof and to verify theoretical information. This kind of test bench in particular makes it possible to measure dust in the turbojet engine.

The document EP 3009826 A1 describes a test bench for a dual-flow turbojet engine. The test bench is a ground infrastructure comprising a corridor receiving the turbojet engine. During the test, the turbojet engine receives various items of equipment specifically provided for the test. A test hood or else a dedicated intake is present among these items of equipment.

As a preliminary step, the test bench must be inspected before the actual test is carried out. In particular, it is necessary to check that the equipment has been properly mounted. It should also be ensured that no foreign objects remain in the corridor of the test bench, without which these objects might be sucked into the turbojet engine or projected through the test bench. Considerable damage occurs in such a case. Even more importantly, it is necessary to ensure that no person remains in the test bench.

All of these checks require time and increase as the test bench becomes longer. The complexity of the test bench adds uncertainty in terms of the accuracy of the checking. Dead angles from the control room reduce the reliability of the checks.

Although great strides have been made in the area of testing of turbine engines, many shortcomings remain.

DETAILED DESCRIPTION OF THE PREFERRED EMBODIMENT

Figure 1:
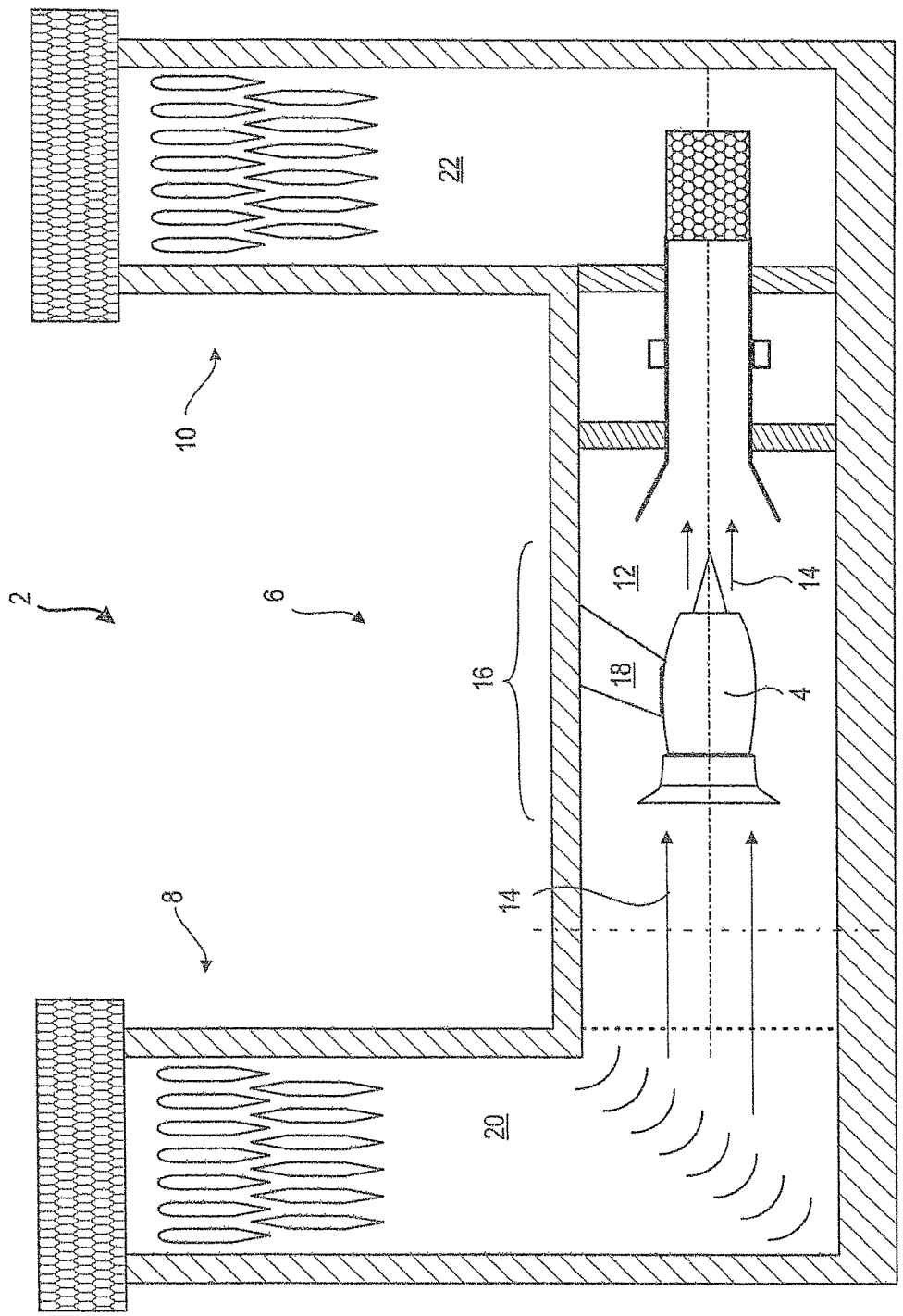
FIG. 1 depicts a test bench according to the invention.

The present application aims to solve at least one of the problems presented by the prior art. More specifically, the aim of the present application lies in improving the safety of testing of a turbine engine. The aim of the present application also lies in optimising the speed and reliability of a turbine engine test.

The subject matter of the present application lies in a method for testing a turbine engine in a test bench, the method comprising the following steps: (a) visual inspection; (b) testing of the turbine engine in the test bench; which is noteworthy in that the test bench comprises an augmented-reality system performing the step of (a) visual inspection in the test bench in order to detect any possible anomaly of a first type; the method performing the step of (b) testing only in the absence of an anomaly of the first type identified by the augmented-reality system.

According to an advantageous mode of the invention, during the step of (a) inspection, feature points are checked inside the test bench in order to detect one or more anomalies of the first type.

According to an advantageous mode of the invention, during the step of (a) inspection, the augmented-reality system compares the actual test bench and/or the actual turbine engine with one or more virtual images contained in a database.

According to an advantageous mode of the invention, the database contains virtual images of intruding elements, and during the step of (a) inspection, the system confirms the absence of intrusion; and the system signals an anomaly of the first type in the case that an intrusion is detected.

According to an advantageous mode of the invention, during the step of (a) inspection, the augmented-reality system produces a virtual image which it compares with a virtual image that is free of an anomaly of the first type.

Items of test equipment are placed in the test bench, especially on the turbine engine, the step of (a) inspection comprising inspection of said items of test equipment.

According to an advantageous mode of the invention, the step of (a) inspection comprises an inspection of sensors inside the test bench.

According to an advantageous mode of the invention, the step of (a) inspection comprises a succession of steps of checking different parameters, and the method possibly continues the succession of checking steps only in the absence of an anomaly of the first type.

According to an advantageous mode of the invention, the step of (a) inspection comprises detecting at least one anomaly of a second type, the method performing the step of (b) testing in the presence of at least one or more anomalies of the second type.

According to an advantageous mode of the invention, the test bench comprises a corridor in which the turbine engine is disposed during the step of (a) inspection and/or during the step of (b) testing, the step of (a) inspection being at least partially carried out by an operator in said corridor.

According to an advantageous mode of the invention, the test bench comprises a test control room, for example adjoining the corridor, the step of (a) inspection being at least partially carried out by an operator in said room.

According to an advantageous mode of the invention, during the step of (b) testing, the augmented-reality system displays a temperature of a flow passing through the test bench, and/or a flow rate of a flow passing through the test bench, and/or a temperature of a flow passing through the test bench.

According to an advantageous mode of the invention, during the step of (b) testing, the augmented-reality system displays a vibration level in the test bench, especially of an item of test equipment and/or of the turbine engine.

According to an advantageous mode of the invention, the augmented-reality system comprises a display module which displays an image to a user, especially an alert signal in the case that an anomaly of the first type is detected.

According to an advantageous mode of the invention, the turbine engine is visible from the display module.

According to an advantageous mode of the invention, during the step of (a) inspection, the turbine engine and the display module are less than 50 m apart, or less than 20 m or 10 m apart.

According to an advantageous mode of the invention, the augmented-reality system comprises at least one or more cameras filming the turbine engine during the step of (a) inspection, one camera possibly being integrated into the display module.

According to an advantageous mode of the invention, the turbine engine is a turbojet engine or a turboprop adapted to generate a blast of propulsion, for example for propelling an aircraft.

According to an advantageous mode of the invention, the augmented-reality system carries out an analysis continuously and/or in real time.

According to an advantageous mode of the invention, the step of (a) inspection is carried out by human means in addition to by the augmented-reality system.

According to an advantageous mode of the invention, the step of (a) inspection comprises an inspection of the test bench and/or of the turbine engine, and/or of test sensors on the turbine engine.

According to an advantageous mode of the invention, the step of (b) testing comprises start-up of the turbine engine.

According to an advantageous mode of the invention, the step of (b) testing starts up after the start-up, and/or after the end of the step of (a) inspection, said steps possibly being performed simultaneously, optionally simultaneously in part.

According to an advantageous mode of the invention, the items of test equipment comprise a test hood for a turbine engine, and/or a turbine engine air intake.

According to an advantageous mode of the invention, when the augmented-reality system identifies an anomaly of the first type, the step of (b) testing is interrupted or inhibited.

According to an advantageous mode of the invention, the method stops the step of (a) inspection and/or the step of (b) testing when an anomaly of the first type is detected.

According to an advantageous mode of the invention, the augmented-reality system remains active during the step of (b) testing, and continues the visual inspection of the test bench during the step of (b) testing.

The subject matter of the present application also lies in a method for testing a turbine engine in a test bench, the method comprising the following steps: (a) visual inspection; (b) testing of the turbine engine in the test bench; which is noteworthy in that the test bench comprises an augmented-reality system performing the step of (a) visual inspection in order to detect in the test bench any possible pre-test anomaly of a first type, for example in regard to the test bench and/or the turbine engine; detection of an anomaly of the first type blocking the start-up of the step of (b) testing, and/or the method performing the step of (b) testing only in the absence of an anomaly of the first type.

The subject matter of the present application also lies in a test bench for a turbine engine, which is noteworthy in that it comprises an augmented-reality system configured to carry out an internal visual inspection in the test bench in order to detect at least one anomaly of a first type; the test bench further being configured to perform a test of the turbine engine only in the absence of an anomaly of the first type identified by the augmented-reality system.

According to an advantageous mode of the invention, the test bench comprises at least 100 sensors, or at least 1000 sensors, or at least 10000 sensors.

According to an advantageous mode of the invention, the test bench comprises a collection tube downstream of the turbine engine, in particular for collecting the blast of propulsion.

According to an advantageous mode of the invention, the length of the corridor is equal to or greater than 20 m, 40 m or 70 m. The length of the corridor may be measured in a straight line.

According to an advantageous mode of the invention, the corridor has a passage cross section of at least 4 m$^2$, or 25 m$^2$, or 50 m$^2$ or 100 m$^2$, for example at the level of the turbine engine.

According to an advantageous mode of the invention, the turbine engine is able to exert a thrust of equal to or greater than 20 kN, or 80 kN, or 200 kN or 500 kN. The fixing arm is possibly designed to withstand corresponding forces.

The subject matter of the present application also lies in a computer program comprising instructions for executing the steps of the test method according to the invention.

The subject matter of the present application also lies in a computer on which is recorded a computer program comprising instructions for executing steps of the test method according to the invention, when said program is executed by a computer connected to at least one camera configured to film part or all of the test bench.

In a general manner, the advantageous modes of each subject matter of the present application are equally applicable to other subject matters of the invention. In so far as possible, each subject matter of the present application may be combined with the other subject matters.

The present application provides greater safety for the test since electronic means accompany the operator responsible for the inspection. The camera in the augmented-reality system is more sensitive than the human eye, enabling an abnormal case to be detected more rapidly, more accurately and with greater certainty.

The augmented-reality system recognizes the different elements to be checked at the same time as the user when said augmented-reality system inspects them. This double checking sharply reduces the likelihood of a danger being missed since defects in the modes of checking are mutually corrected and compensated.

Moreover, the present application makes it possible to reduce the time required for the inspection since a simple camera sweep of the zones to be checked makes it possible to determine positioning in terms of the configuration of the test bench. Moreover, movement of the operator tends to lead to zones being swept several times since the augmented-reality system functions continuously. Once again, this feature tends to produce a reduction in inspection defects.

FIG. 1 depicts, in a simplified manner, a test bench 2 for a turbine engine 4. This instance relates to a dual-flow turbojet engine, for example for propelling an aircraft. The turbine engine may comprise a blower propelling air through the test bench 2, this blast moreover generating thrust enabling propulsion of an aircraft.

The test bench 2 forms an infrastructure and a construction. It comprises a passage 6 with an intake 8 and an outlet 10. The passage 6 may comprise a corridor 12 substantially elongated in a straight line and possibly horizontal. The length thereof may be equal to or greater than 80 m. The length of the corridor 12 allows circulation in a straight line of a flow of air 14 or circulation of air 14 passing through the passage 6. This flow of air 14 circulates through the test bench 2 because of the blast of the turbine engine 4.

In order to limit flow resistance, especially the intake of a flow of air 14 into the turbojet engine 4, the corridor 12 may have a passage cross section of equal to or greater than 50 m². The passage cross section, or open cross section, may be measured upstream of the fixing zone 16 intended to receive the turbine engine 4. The fixing zone 16 may be a section of the corridor 12 along the length thereof. The passage cross section may be apparent over at least a quarter of the length of the corridor 12, preferably over the majority of the length thereof.

The fixing zone 16 is possibly provided with a fixing arm 18 where the turbine engine 4 is mounted. The arm 18 may extend vertically from the ceiling of the corridor 12 in the manner of a column or a pole. The arm 18 allows the turbojet engine 4 to be mounted with an offset, and to centre the latter in the middle of the corridor 12. The centering is vertical and horizontal.

The corridor 12 may be delimited by vertical stacks (20; 22) at the intake 8 and the outlet 10. The "U"-shaped configuration detailed here is not essential; other configurations may be envisaged, for example without stacks.

According to a variant of the invention, the test bench may be an open-air test bench. It may comprise an open-air test bench such as described in the document EP 3 009 826 A1.

The test bench 2 may be provided with energy recovery systems. Shutters may equally be arranged through the test bench in order to extinguish a fire therein.

Figure 2:
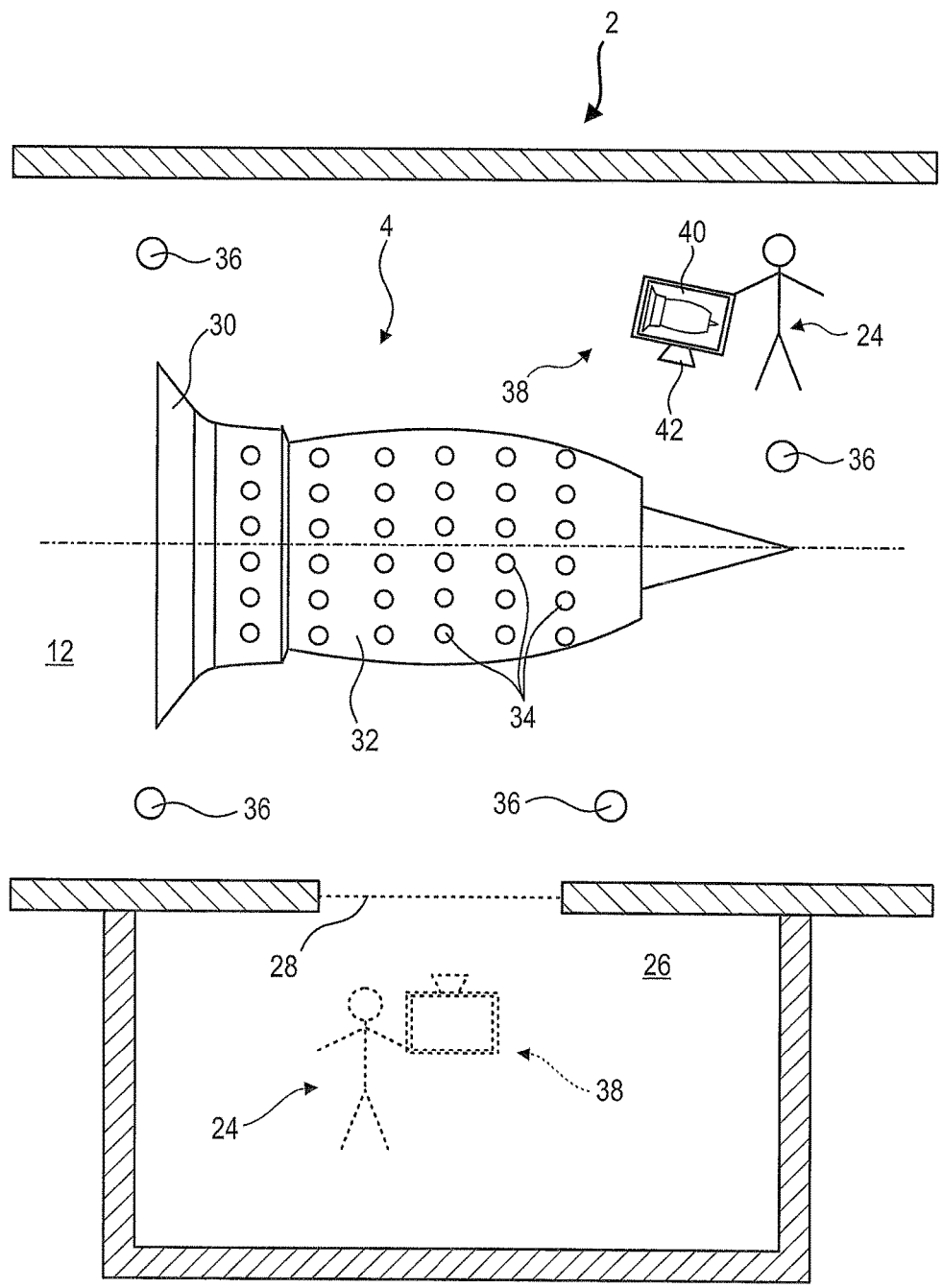
FIG. 2 is a schematic diagram of a portion of the test bench in FIG. 1.

FIG. 2 is a view from above of the test bench 2 according to the invention. The fixing arm is not depicted. One or more operators 24 perform an inspection before starting up the test of the turbine engine 4.

The inspection may be conducted by an operator 24 from the corridor 12, and/or from a control room 26 adjoining the corridor 12. The control room 26 possibly comprises a window 28 offering a visual check on the turbine engine 4 during testing, inspection and installation thereof in the bench 2.

In order to test the turbine engine 4, it may be equipped with certain items of test equipment. It may receive an intake 30 in the shape of a dome. It may equally receive one or more test hoods 32. These may be external hoods in contact with the environment of the turbine engine 4, or internal hoods in contact with the secondary flow and/or the primary flow circulating in the turbine engine 4. These test hoods 32 may be provided with first sensors 34 making it possible to obtain measurements specific to the turbine engine during the tests. In addition, second sensors 36 may be provided in the test bench 2 at a distance from the turbine engine.

These sensors (34; 36) make it possible to provide information, for example a flow rate of a flow. They may equally provide information regarding the temperature of the flowing air. The pressure may also be measured. Vibrations may also be measured in order to determine a sound level, for example.

The safety of the test depends on correct mounting of the items of test equipment. The identity of these items of equipment should be checked and the correct positioning thereof with respect to the turbine engine should be checked. It is also necessary to check the positions of the first sensors 34 and the second sensors 36. The state of functioning of these sensors is also optionally checked.

To these ends, an augmented-reality system 38 is made available to the operator 24. This system 38 may be portable. It may comprise a display module 40 or a graphic unit such as a tablet or a headset with a glass projecting an image towards the operator. The augmented-reality system 38 may comprise a camera 42 allowing the test bench 2 to be filmed. The camera 42 makes it possible to film the various sensors (34; 36), the turbine engine 4 and the items of test equipment, and to produce virtual images therefrom.

The augmented-reality system 38 may comprise a computer with a computer program which accurately produces the virtual images. The computer program also makes it possible to superimpose data on the virtual images produced in real time. The added data may provide information on the conformity of the test bench before a test is started up, or in order to proceed with a test. The added data makes it possible to identify anomalies on the items of test equipment, such as incorrect positioning of a test hood 32 which is not correctly closed up. In such a case, the display module 40 issues an alert signal, for example superimposed on the item of test equipment concerned in the virtual image produced.

The augmented-reality system 38 may optionally be used during the testing step. At that point, the superimposed, and therefore added, data may provide information on the sensors (34; 36). It is thus possible to add data relating to the temperature, pressure, flow rate and vibrations.

The presence of a camera 42 on the display module 40 remains an optional aspect of the invention. Specifically, the camera may be fixed to the passage 12. Optionally, the system comprises several cameras in order to create virtual inspection images. The system comprises means for determining the position and orientation of the display module 40 and adapts the virtual image as a function of the field of vision of this display module 40.

Figure 3:
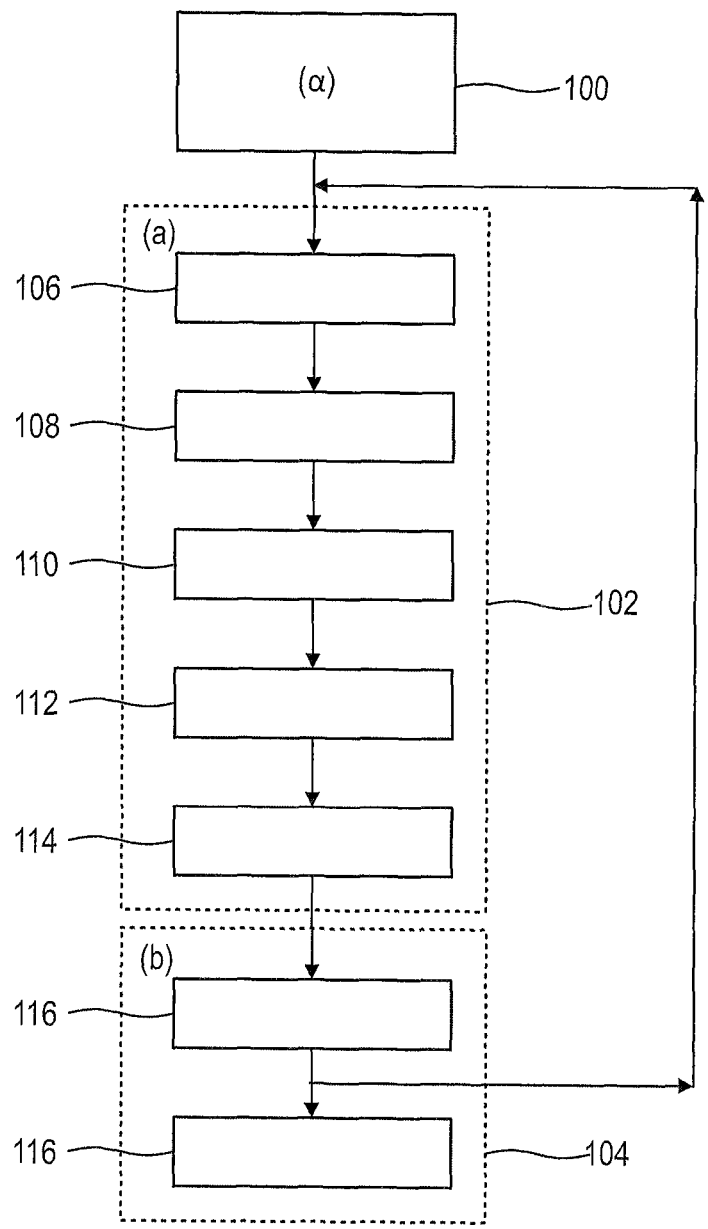
FIG. 3 illustrates a diagram of the test method according to the invention.

FIG. 3 illustrates a diagram of the method for testing the turbine engine. This method may be conducted with the aid of the augmented-reality system 38 illustrated in FIG. 2, for example in the test bench in FIGS. 1 and 2.

The method may comprise the following steps, possibly carried out in the following order:
  (a) installation 100 of the turbine engine in the test bench;
  (a) visual inspection 102 of the conformity of the test conditions in the test bench with the aid of the augmented-reality system;
  (b) testing 104 of the turbine engine in the test bench.

The step of (a) installation 100 comprises fixing of the turbine engine on or under a test support thereof, for example under the fixing arm. Optionally, this step comprises replacing the standard hoods of the turbine engine with test hoods. Finally, an intake may be added. The various sensors of the test hoods may be connected to a central unit that gathers the test data. These sensors may communicate with the augmented-reality system.

The step of (a) visual inspection 102 is conducted by virtue of the augmented-reality system which provides assisted checking. In order to carry out the inspection, the camera scans a part or all of the test zone and analyses the image generated. This checking may be conducted by comparing actual reference points with images which these points should show in a conforming test situation. These points may be on the turbine engine and/or on a surface of the corridor. The colour and the brightness of the points may be controlled. Conforming images of these points may be contained in a database which may equally be adapted to different models of turbine engines. There is an anomaly when a point is non-conforming; for example, an anomaly of a first type, possibly a major anomaly prohibiting the test from being carried out.

Alternatively or additionally, the augmented-reality system may seek to identify the presence of certain entities in the bench. The database may contain reference virtual images of human beings, tools used for mounting the turbine engine, and sensors. In the case where a tool or a person is detected, an alarm signal is sent. The system may check the images of the sensors present. The situation is conforming if they correspond to those required for predefined test conditions. Conversely, an alarm is triggered if an identified sensor does not belong to all of those required.

The augmented-reality system may communicate with the sensors. It may display whether they are operational or faulty. This kind of fault may be equated to an anomaly of a second type. If the number of these anomalies remains equal to or lower than a predetermined threshold, the step of (b) testing 104 may still be carried out.

The step of (a) visual inspection 102 may comprise a succession of intermediate steps. For example, the intermediate steps may comprise:
checking the test hoods 106;
checking the intake 108;
checking the first sensors 110;
checking the second sensors 112;
checking the absence 114 of foreign bodies in the test bench, and especially in the corridor.

If these checks result in an actual conforming situation, the method may conduct the step of (b) testing 104. It should be noted that the checks may be carried out between several intermediate test steps 116, or during the test in which the turbine engine is operational. According to an option of the invention, the augmented-reality system may remain active during the step of (b) testing. The inspection of the test bench and of the turbine engine is then continued during operation of the latter. For example, a presence in the bench during the test or possibly the opening of a door may be detected, for example. Furthermore, it is also possible to ascertain a movement of a fixed element which is supposed to remain immobile. By way of example, it is possible to detect a movement of a flap at the intake or outlet, or the movement of a fixture of an item of engine equipment. Thereupon, the system is able to anticipate detachment of a fixture, for example of a catch, also called a "latch". The system can also detect the suspected appearance of smoke, or the start of a fire. In response to the abovementioned incidents, the augmented-reality system may emit an alarm signal. It may also interact with the test bench in such a way as to automatically interrupt the test during which the anomaly or anomalies of the first type has/have been detected.

The test may be interrupted following an anomaly of the first type and/or continue despite the appearance of an anomaly of the second type. The method may be iterative and/or operate in a loop.

I claim:

1. A method for testing in running a turbine engine in a test bench, the method comprising:
   (a) visual inspection; and
   (b) testing of the turbine engine in the test bench;
   wherein the test bench comprises:
   an augmented-reality system performing the step of (a) visual inspection
   in the test bench in order to detect any possible anomaly of a first type;
   the method only performing the step of (b) testing in the absence of an anomaly of the first type identified by the augmented-reality system; and
   wherein items of test equipment are placed in the test bench and on the turbine engine, the step of (a) inspection comprising:
   inspection of identity and positioning of said items of test equipment.

2. The method for testing a turbine engine according to claim 1, wherein during the step of (a) inspection, feature points are checked inside the test bench in order to detect one or more anomalies of the first type.

3. The method for testing a turbine engine according to claim 1, wherein the augmented-reality system comprises:
   a database with one or more virtual images; and
   during the step of (a) inspection the augmented-reality system compares the test bench and/or the turbine engine with said one or more virtual images so as to identify an anomaly of the first type.

4. The method for testing a turbine engine according to claim 3, wherein the database contains virtual images of intruding elements, and during the step of (a) inspection, the system checks the absence of intruding elements and the augmented-reality system signals an anomaly of the first type in the case that an intruding element is detected.

5. The method for testing a turbine engine according to claim 1, wherein during the step of (a) inspection, the augmented-reality system produces a virtual image which it compares with a virtual image that is free of an anomaly of the first type.

6. The method for testing a turbine engine according to claim 1, wherein the step of (a) inspection comprises:
   an inspection of sensors inside the test bench.

7. The method for testing a turbine engine according to claim 1, wherein the step of (a) inspection comprises:
   a succession of steps of checking different parameters, and the method continues the succession of checking steps only in the absence of an anomaly of the first type, and stops the succession of checking steps if an anomaly of the first type is detected.

8. The method for testing a turbine engine according to claim 1, wherein the test bench comprises:
   a corridor in which the turbine engine is disposed during the step of (a) inspection and/or during the step of (b) testing, the step of (a) inspection being at least partially carried out by an operator in said corridor.

9. The method for testing a turbine engine according to claim 8, wherein the test bench comprises:
   a test control room adjoining the corridor, the step of (a) inspection being at least partially carried out by an operator in said room.

10. The method for testing a turbine engine according to claim 1, wherein during the step of (b) testing, the augmented-reality system displays a temperature of a flow passing through the test bench, and a flow rate of a flow passing through the test bench, and a temperature of a flow passing through the test bench.

11. The method for testing a turbine engine according to claim 1, wherein during the step of (b) testing, the augmented-reality system displays a vibration level in the test bench.

12. The method for testing a turbine engine according to claim 1, wherein the augmented-reality system comprises:
   a display module which displays an image to a user, said image comprising:
   an alert signal in the case that an anomaly of the first type is detected.

13. The method for testing a turbine engine according to claim 12, wherein the turbine engine is visible from the display module.

14. The method for testing a turbine engine according to claim 1, wherein the augmented-reality system comprises:
   at least one or more cameras filming the turbine engine during the step of (a) inspection.

15. The method for testing a turbine engine according to claim 1, wherein the turbine engine is a turbojet engine or a turboprop adapted to generate an aircraft propulsive jet.

16. The method for testing a turbine engine according to claim 1, wherein the augmented-reality system remains active during the step of (b) testing, and continues the visual inspection of the test bench during the step of (b) testing.

17. A method for testing in running a turbine engine in a test bench, the method comprising the following steps:
   (a) visual inspection; and
   (b) testing of the turbine engine in the test bench;
   wherein the test bench comprises:
      an augmented-reality system performing the step of (a) visual inspection in the test bench in order to detect any possible anomaly of a first type, and any possible anomaly of a second type;
   the method performing the step of (b) testing in the absence of an anomaly of the first type, and in the presence of an anomaly of the second type identified by the augmented-reality system; and
   wherein items of test equipment are placed in the test bench and on the turbine engine, the step of (a) inspection comprising:
      inspection of identity and positioning of said items of test equipment.

18. A test bench for a turbine engine, comprising:
   an augmented-reality system configured to carry out an internal visual inspection in the test bench in order to detect at least one anomaly of a first type, the test bench comprising:
      a computer program being configured to perform a running test of the turbine engine in the absence of an anomaly of the first type identified by the augmented-reality system which is designed and configured to inspect an identity and a positioning of items of test equipment placed in the test bench and on the turbine engine, and being configured to prevent from performing the test of the turbine engine if an anomaly of the first type is detected by the augmented-reality system.

19. A test bench according to claim 18, further comprising:
   at least 100 sensors;
   at least 1,000 sensors; or
   at least 10,000 sensors.

* * * * *